United States Patent
Bugner et al.

(10) Patent No.: US 9,430,025 B2
(45) Date of Patent: Aug. 30, 2016

(54) METHOD FOR TEMPORARY OPERATION OF AN AUTOMATED ANALYSIS DEVICE IN A STANDBY MODE

(71) Applicant: Siemens Healthcare Diagnostics Products GmbH, Marburg (DE)

(72) Inventors: Dirk Bugner, Mainz (DE); Markus Preidel, Frankfurt (DE); Klaus Proch, Reiskirchen (DE); Holger Pufahl, Liederbach (DE)

(73) Assignee: SIEMENS HEALTHCARE DIAGNOSTICS PRODUCTS GMBH, Marburg (DE)

( * ) Notice: Subject to any disclaimer, the term of this patent is extended or adjusted under 35 U.S.C. 154(b) by 253 days.

(21) Appl. No.: 14/092,878

(22) Filed: Nov. 27, 2013

(65) Prior Publication Data

US 2014/0149778 A1    May 29, 2014

(30) Foreign Application Priority Data

Nov. 28, 2012 (EP) .................... 12194558

(51) Int. Cl.
*G01N 35/00* (2006.01)
*G06F 1/32* (2006.01)

(52) U.S. Cl.
CPC ....... *G06F 1/3234* (2013.01); *G01N 35/00584* (2013.01); *G06F 1/3206* (2013.01); *G06F 1/3293* (2013.01); *Y02B 60/121* (2013.01)

(58) Field of Classification Search
None
See application file for complete search history.

(56) References Cited

U.S. PATENT DOCUMENTS

| | | | |
|---|---|---|---|
| 5,721,936 A | 2/1998 | Kikinis et al. | |
| 6,631,474 B1 * | 10/2003 | Cai | G06F 1/3203 713/300 |
| 2002/0049921 A1 | 4/2002 | Akiyama | |
| 2004/0257898 A1 | 12/2004 | Ozawa et al. | |
| 2006/0011111 A1 * | 1/2006 | Stoddard | E05G 1/00 109/1 R |
| 2011/0055434 A1 * | 3/2011 | Pyers | G06F 1/3203 710/14 |
| 2013/0038615 A1 * | 2/2013 | Hendry | G06F 1/3206 345/502 |
| 2013/0243652 A1 * | 9/2013 | Nishigaki | G01N 35/00584 422/68.1 |
| 2014/0136829 A1 * | 5/2014 | Liang | G11B 19/041 713/2 |

FOREIGN PATENT DOCUMENTS

WO    2012/070557 A1    5/2012

OTHER PUBLICATIONS

European Search Report and Written Opinion of European patent Application No. 12194558.8 dated Jun. 13, 2013 (6 Pages).

* cited by examiner

*Primary Examiner* — Thomas Lee
*Assistant Examiner* — Danny Chan
(74) *Attorney, Agent, or Firm* — Dugan & Dugan, PC

(57) ABSTRACT

The present invention relates to an automated analysis device (1) and a method for temporary, energy-saving operation of the analysis device (1) in a standby mode, the analysis device (1) comprising a central control unit (6) and a standby control unit (24).

18 Claims, 2 Drawing Sheets

METHOD FOR TEMPORARY OPERATION OF AN AUTOMATED ANALYSIS DEVICE IN A STANDBY MODE

Figure 1:
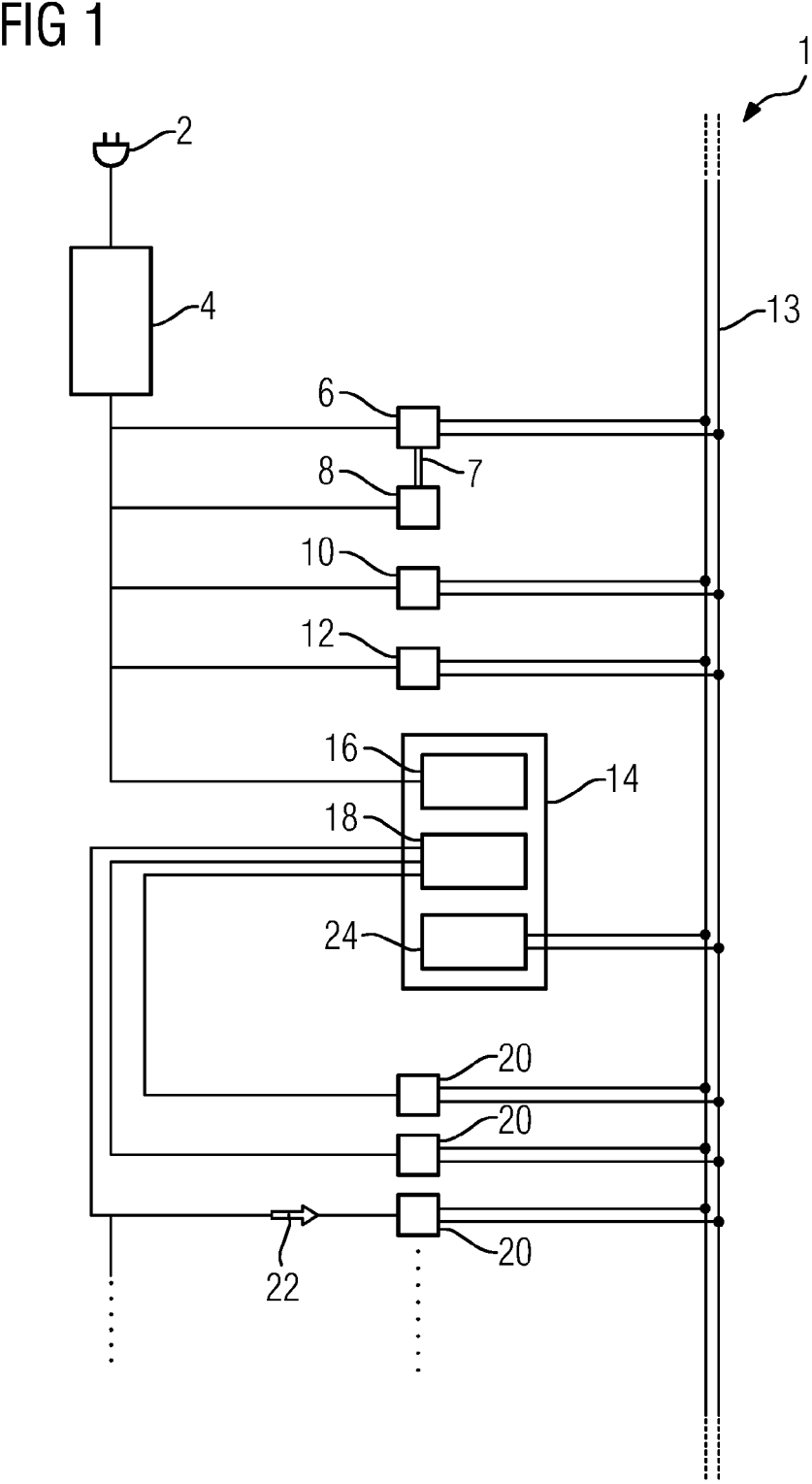

The invention lies in the field of in-vitro diagnostics and relates to an automated analysis device and a method for temporary, energy-saving operation of the analysis device in a standby mode, the analysis device comprising a central control unit and a standby control unit.

Numerous detection and analysis methods for determining physiological parameters in bodily fluid samples such as blood, plasma, serum or urine or in other biological samples are carried out automatically these days in appropriate analysis devices.

Current analysis devices are able to carry out a multiplicity of different detection reactions and analyses on a multiplicity of samples. Conventional analysis devices, as are used in clinical laboratories or in blood banks, usually comprise an area for supplying sample vessels which contain the primary samples to be analyzed. In order to feed the sample vessels into the analysis device, provision is usually made for a transport system which, initially, transports the sample vessels to a sample identification apparatus which detects sample-specific information attached to a sample vessel and transmits it to a storage unit. The sample vessels are subsequently transported to a sample removal station. With the aid of a sample pipetting apparatus, at least one aliquot of the sample liquid is taken from a sample vessel at said location and transferred into a reaction vessel.

The reaction vessels are, in general, disposable cuvettes, which are stored in a cuvette container in the analysis device and automatically transferred from the storage container into defined take-up positions. However, there are also devices in which the cuvettes are used a number of times by virtue of being washed prior to the next use. The reagents required for providing different, test-specific reaction mixtures are situated in reagent containers that are stored in a reagent station. The reagent containers are supplied to the analysis device either in an automated or manual fashion.

The reagent station usually comprises a cooling unit in order to ensure a shelf life of the reagents that is as long as possible. An aliquot of one or more reagents is transferred into a reaction vessel, in which the sample to be examined is already situated, with the aid of a reagent pipetting apparatus, which incidentally often has a heater. Depending on the type of biochemical reaction started by the addition of the reagents to a sample, incubation times of the reaction mixture may be required to vary in length. In any case, the reaction vessel with the reaction mixture is finally supplied to a measurement system which measures a physical property of the reaction mixture.

Measurement systems based on photometric (e.g. turbidimetric, nephelometric, fluorometric or luminometric) or radiometric measurement principles are particularly widespread. These methods enable the qualitative and quantitative detection of analytes in liquid samples without having to provide additional separation steps. Clinically relevant parameters, such as e.g. the concentration or the activity of an analyte, are often determined by virtue of an aliquot of a bodily fluid of a patient being mixed, simultaneously or in succession, with one or more test reagents in the reaction vessel, as a result of which a biochemical reaction which brings about a measurable change in an optical property of the test mixture is started.

The measurement system in turn transmits the measurement result to a storage unit and evaluates it. Subsequently, the analysis device supplies sample-specific measurement values to a user by means of an output medium such as e.g. a monitor, a printer or a network connection.

In addition to the above-described essential functions, an automated analysis device comprises a multiplicity of further components, such as, for example, stepper motors for driving pipetting apparatuses, cuvette grippers or other movable apparatuses, temperature sensors, pressure sensors, motion sensors, liquid-level detectors, heating elements, ventilators, light sources and many more. The highly complex interaction of all components and functions of an automated analysis device is controlled by a central control unit, which is usually in the form of a personal computer with a storage medium, computational unit, monitor and keyboard.

In order to operate all these functions and components, electric energy needs to be supplied to the automated analysis device. In particular, the power consumption of the analysis device when not carrying out tests but when being kept in standby is problematic. When the analysis device is not in use, i.e. when no analyses are required, it is conventional to put analysis devices into a standby mode. To this end, various functions of the device such as e.g. movable apparatuses, heaters or light sources are switched off and the central control unit is put into an internal rest mode in order to reduce the power consumption.

However, it is disadvantageous that restarting the operating mode takes ever longer the more components of the analysis device are switched off. However, since restarting the operating mode must take as little time as possible, particularly in clinical laboratories which have to be prepared at all times for processing emergency samples, it typically is the case that all electronics of the device are kept energized such that the device can be started up again very quickly. However, the central control unit, which is typically designed as a personal computer, remains energized in all cases. This results in significant power consumption of the device, even at times when it is not in use.

It is therefore an object of the invention to provide a method by means of which an automated analysis device can temporarily be operated in a standby mode, which significantly reduces the power consumption and, at the same time, enables the operating mode to be restarted as quickly as possible.

This object is achieved by virtue of the automated analysis device being provided with a standby control unit and the method comprising the following steps:
  starting up the standby control unit,
  storing at least one established system state of the automated analysis device in the central control unit, and
  shutting down the central control unit.

In a preferred embodiment of the method, the standby control unit monitors a number of operating parameters during the standby mode for a deviation from a predetermined intended value.

A further subject of the present invention relates to a method for restoring the operating mode in an automated analysis device, which is operated in a standby mode using the above-described method according to the invention. The method for restoring the operating mode advantageously comprises the following additional method steps:
  restarting the central control unit and
  loading the operating parameters monitored by the standby control unit into the central control unit.

Here, the invention is based on the idea that power consumption could be reduced during a period of non-use if, in particular, it were possible to completely shut down the central control unit. To this end, provision is made for a dedicated standby control unit which is independent of the central control unit. Since the standby control unit need not control analyses, it can have a substantially simpler and more power-saving design than the central control unit. However, in this case it is disadvantageous that the system states, i.e. the states of the individual components or functional units of the system, are also lost when the central control unit is switched off. Said states firstly have to be reestablished by means of a complicated procedure when restarting the system, as a result of which the time taken for the restart becomes significantly longer. Hence the system states are stored prior to deactivating the central control unit, the standby control unit is started up and the central control unit shut down.

The term "central control unit" should be understood to mean a control unit configured such that it controls all functional units of the automated analysis device when said device is in the so-called operating mode. In the operating mode, all functional units of the device are active or can at least be used immediately. The central control unit is preferably designed as a personal computer.

The term "standby control unit" should be understood to mean a control unit configured such that it only controls a subset of all functional units of the automated analysis device when said device is in a so-called standby mode. In the standby mode, only a subset of all functional units of the automated analysis device is active and the device as a whole cannot be used immediately, i.e. it is not possible to immediately carry out analyses. The standby control unit is preferably designed as programmable microcontroller or digital control module, which is arranged on a printed circuit board and is only connected to a subset of the functional units of the automated analysis device.

In a preferred embodiment, the automated analysis device, which has a central control unit, is equipped with a standby control unit configured such that it monitors a number of operating parameters for a deviation from a predetermined intended value after the central control unit is shut down.

By way of example, the temperature in the cooling unit can be checked during the standby mode in respect of remaining within a predetermined temperature interval. Appropriate sensors can also check whether housing parts were opened during the standby mode. Possible deviations from the intended value are stored in the standby control unit and transmitted to the central control unit during the restart. Here, said deviations can be processed further and the validity of the stored system states can be checked on the basis of the identified deviations.

The standby control unit advantageously controls an electric switch which separates the central control unit from the voltage supply. This separation takes place within the course of shutting down the central control unit during the transition into the standby mode.

Modern automated analysis devices often comprise a cooling unit for reagents employed in the analyses. In an advantageous embodiment, the standby control unit also operates the cooling unit. As a result, there is no longer the need to remove the reagents at times, e.g. overnight, at which no analyses are carried out. The reagents remain in the device and are continued to be cooled during the standby mode. They are immediately available upon restart.

As already described above, automated analysis devices often furthermore comprise sample and/or reagent storages. These typically contain the samples and the reagents employed for the analysis. Here the central control unit needs to know which samples and which reagents are stored at which positions in the storage so that automated processing is possible. Hence, in an advantageous embodiment, the system state stored in the central control unit is a load state of the sample and/or reagent storage. Deviating load states can be loaded into the central control unit from the standby control unit upon restart, i.e. during the transition from the standby mode into the operating mode. Otherwise it would be necessary to establish this with much effort by the automated removal of each individual reagent container and by reading out e.g. a barcode printed thereon, which would significantly slow down the restart process.

The automated analysis device furthermore often comprises a consumable and/or waste storage. Reaction vessels and pipette tips are typical consumables which are stored in large numbers in appropriate storage containers in the device and which are disposed of in a waste container after a single use. The system state stored in the central control unit is therefore advantageously a load state of a storage container for a consumable, such as e.g. reaction vessels or pipette tips, and/or of a waste container. Deviating load states can be loaded into the central control unit from the standby control unit upon restart, i.e. during the transition from the standby mode into the operating mode. This avoids it being necessary to check the state of the consumables and of the waste during restart.

The standby control unit can be started up and hence the standby mode can be initiated either actively by a command from a user or after a predetermined period of inactivity of the automated analysis device. The power consumption is likewise reduced by the latter variant since the standby mode is activated even if this is forgotten about by the user.

In an advantageous embodiment, the standby control unit monitors a number of operating parameters for a deviation from a predetermined intended value.

Furthermore, the deviations identified by the standby control unit are advantageously indicated to a user when restarting the central control unit. The user can then assess whether e.g. an opening of the housing was critical to the load state since reagents were removed or whether all that took place was an optical examination. The user can also decide that a temperature deviation, for example, was so small that there is no need to replace the reagents.

Alternatively, the system state can be reestablished following a user input. This is because if the deviations were such that the information stored in the standby control unit is no longer reliable, the corresponding information is reestablished. However, this is not mandatory.

The advantages obtained by the invention consist of, in particular, a separate standby control unit rendering it possible to deactivate the central control unit and further assemblies and functional units such as motors, valves and heaters of the automated analysis device in the standby mode and to achieve significant energy savings thereby. As a result of this, the consumption can be reduced by up to 300 W compared to systems known from the prior art. By storing system states and state changes during the standby mode it is possible to return to the operationally ready state (operating mode), in particular, without renewed time-consuming establishment of a system state. By monitoring relevant operating parameters during the standby mode and by assessing deviations by the user when terminating the standby mode and restarting the automated analysis device, it is possible for this transition to take place in a very safe manner.

Figure 2:
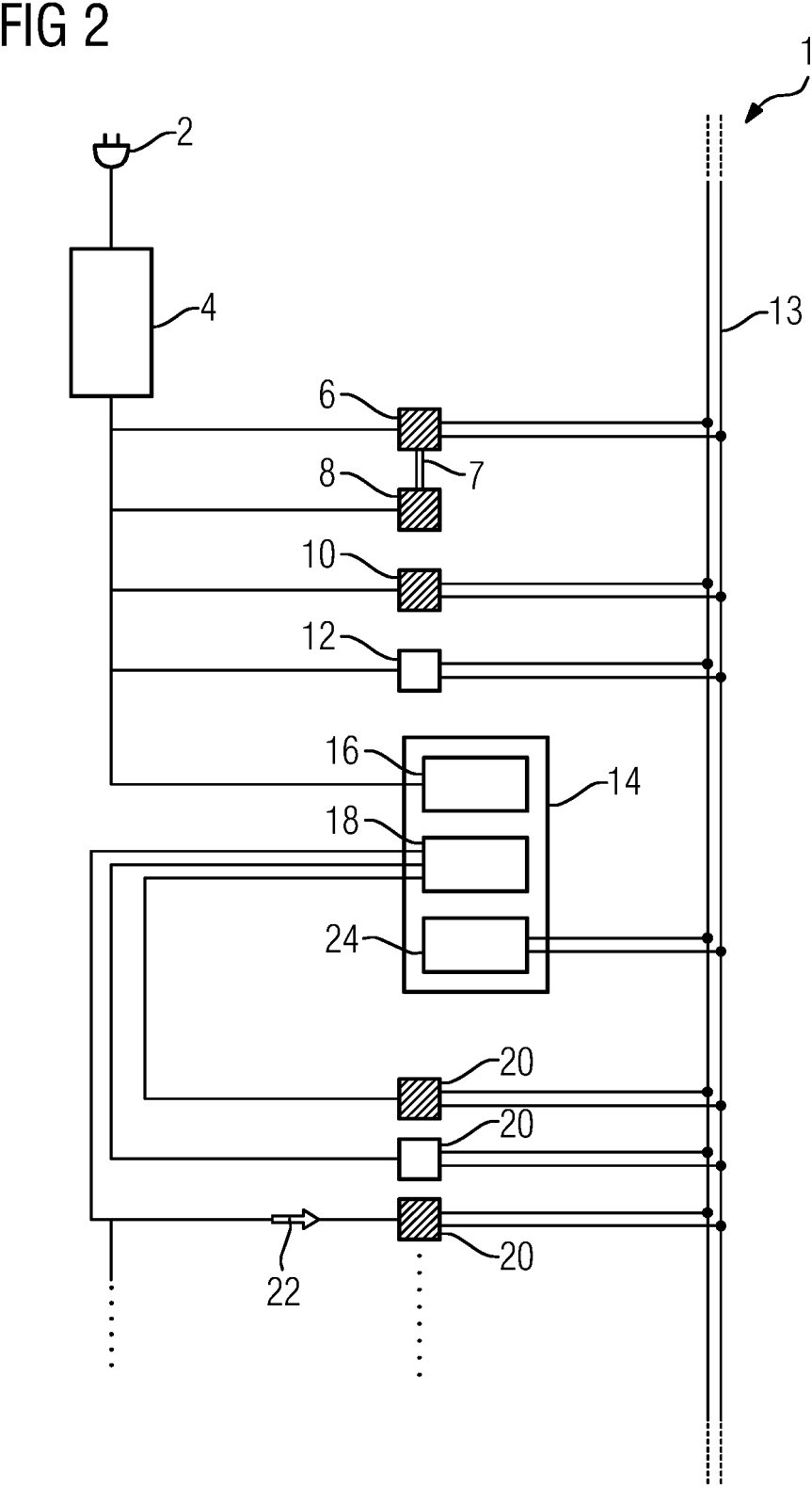

The invention will be explained in more detail on the basis of a drawing. Therein:

FIG. 1 shows a schematic illustration of an automated analysis device in an operating mode and FIG. 2 shows a schematic illustration of an automated analysis device in a standby mode.

The same parts have been provided with the same reference signs in both figures.

FIG. 1 schematically shows the design of an automated analysis device 1. Here, electric supply lines are shown using single lines in the left-hand region of FIG. 1 and data connection lines are shown using double lines in the right-hand region. The automated analysis device 1 has a plug-in connector 2 for the power supply from a plug for 220 V or 110 V AC mains. The plug-in connector 2 is connected to an AC hub 4. The AC hub 4 is connected to those systems of the automated analysis device 1 which are designed for supply with AC voltage.

These systems include the central control unit 6, which is designed as a personal computer, a monitor 8, which is connected to the central control unit by means of a graphics data connection 7 designed as a DVI or VGA cable, a vacuum pump 10 and a cooling unit 12, which, in particular, comprises a refrigerating compressor. In particular, the cooling unit 12 serves to cool a reagent storage (not depicted in any more detail), in which a multiplicity of reagents are stored for various diagnostic tests. These are automatically taken by a removal system (likewise not depicted in any more detail) when required.

A DC hub 14 is connected to the AC hub 4. The former comprises a power supply unit 16 with a rectifier for converting the alternating current from the AC hub 4 into a 24 V DC voltage. The DC hub 14 furthermore comprises an output unit 18, which emits the 24 V DC voltage to various DC-operated modules 20 of the automated analysis device 1.

The DC-operated modules 20 comprise, inter alia, a photometer which is used during the analysis and is rotatably mounted and therefore is supplied by means of a slip ring 22. Furthermore, the DC-operated modules 20 comprise electric motors of the transfer systems for samples, aliquots and reagents and further components. The modules 20 furthermore comprise sensors which monitor the operating states of the automated analysis device, such as e.g. the opening of the housing. If the whole automated analysis device 1 is in operation, the power consumption in the exemplary embodiment lies at approximately 1500 W. In FIG. 1, only three modules 20 are depicted for reasons of clarity.

On the data side, the various components of the automated analysis device 1 are connected by a data bus 13. On the one hand, the data bus 13 transmits control data from the central control unit 6 to the modules 20, the vacuum pump 10 and the cooling unit 12. On the other hand, the data from these components are transmitted to the central control unit 6. These also comprise sensor data which are detected by the sensors respectively associated with these components.

During a phase of non-use of the automated analysis device 1, the central control unit 6 can be put into a rest state. However, the power supply for all the components shown in FIG. 1 remains intact. Even if none of the modules 20 is active, the current input in the exemplary embodiment in this case remains at approximately 500 to 600 W.

In order to further reduce this current input, the automated analysis device 1 has a standby control unit 24. The standby control unit 24 has a comparatively simple design and has a low current input. Unlike the central control unit 6, it is not embodied as a personal computer but merely comprises a printed circuit board with a microcontroller with associated storage medium and appropriate connections to the data bus 13 and to the power supply. The standby control unit 24 is integrated into the housing of the DC hub 14 and can interrupt the power supply to the individual components (e.g. 6, 8, 10 and 12) of the automated analysis device 1 by means of electric switches not shown in any more detail.

The standby mode is activated by a user input on the central control unit 6 or after a period of inactivity of the automated analysis device 1, which can be set on the central control unit 6. To this end, the standby control unit 24 is initially started up. The central control unit 6 then stores a multiplicity of system states, in particular the load and filling state of the reagent storage, the load state of the waste storage and the storages of various consumables such as e.g. cuvettes, pipette tips etc. Any further system states, knowledge of which is required for operating the system, are conceivable.

The central control unit 6 is subsequently shut down. Here, the shutdown comprises not merely a rest state, but the central control unit 6 is separated from the voltage supply by the AC hub 4 by an electric switch that can be controlled by the standby control unit 24. The same applies to the monitor 8 and the vacuum pump 10. Likewise, all bar a few individual modules 20 are separated from the voltage supply by the DC hub 14 by an electric switch that can be controlled by the standby control unit 24.

The standby mode is depicted in FIG. 2, which substantially shows all components from FIG. 1; however, the components separated from the electric supply are shaded in this case. Only a few modules 20, in particular sensors which monitor the access to the housing of the automated analysis device 1, are still active, just like the AC hub 4, the DC hub 14, the cooling unit 12 and naturally the standby control unit 24. Here, the standby control unit 24 is designed such that the operation of the still active components can take place in the standby mode by means of the data bus 13.

The standby control unit 24 monitors the active modules 20, in particular the sensors, and the cooling unit 12 in respect of specific operating parameters for deviations from a predetermined intended value, for example, it monitors the housing in respect of opening or the temperature in the reagent storage. Here, the data bus 13 is also used for the data transmission in the standby mode. Every deviation is logged in the storage medium of the standby control unit 24. In the process, time and type of deviation are recorded. Hence, the power consumption in the exemplary embodiment is restricted to 200 to 250 W in the standby mode.

The automated analysis device 1 can in turn be reactivated into the operating state either by user input by means of a switch associated with the standby control unit 24 or else after a period that can be set in the standby control unit 24 or at a fixed time. Here, the components separated from the power supply are initially resupplied with current and the central control unit 6 is activated. Subsequently, the stored system states are loaded into the central control unit 6 and are therefore directly available and need not be reestablished in a time-consuming manner.

The deviations logged during the standby mode by the standby control unit 24 are likewise transmitted to the central control unit 6. The user is informed if deviations from the intended state have occurred. The user can thus make a decision in respect of keeping the information in relation to the system states.

If no deviations occur or if identified deviations are considered uncritical by the user, the automated analysis device is ready for operation after the activation. All relevant system states, i.e., in particular, status and load states, are correctly reestablished by employing the data stored in the standby control unit 24. This is significantly faster than complete reestablishment.

In the case of deviations evaluated as critical by the user, the affected units are, depending on state, initialized or the load is reestablished. Thus, for example, reagents can be re-identified or, if the permissible storage temperature is overshot or undershot for a relatively long time, they can be disposed of.

LIST OF REFERENCE SIGNS

1 Automated analysis device
2 Plug-in connector
4 AC hub
6 Central control unit
7 Graphics data connection
8 Monitor
10 Vacuum pump
12 Cooling unit
13 Data bus
14 DC hub
16 Power supply unit
18 Output unit
20 Module
22 Slip ring
24 Standby control unit

The invention claimed is:

1. A method for operating an automated analysis device in a standby mode, the automated analysis device comprising a central control unit and a standby control unit, the method having the following method steps:
   providing AC power from an AC hub to the central control unit,
   operating a cooling unit for reagents with the central control unit,
   providing the AC power from the AC hub to a DC hub comprising a power supply unit,
   providing DC power from the power supply unit to the standby control unit,
   starting up the standby control unit,
   operating the cooling unit with the standby control unit,
   storing at least one established system state of the automated analysis device in the central control unit, and
   shutting down the central control unit.

2. The method as claimed in claim 1, wherein the central control unit is shut down by the central control unit being separated from the AC hub by an electric switch controlled by the standby control unit.

3. The method as claimed in one of the preceding claims, wherein the standby control unit monitors a temperature in the cooling unit.

4. The method as claimed in claim 1, in which the automated analysis device comprises a sample and/or reagent storage and the system state is a load state of the sample and/or reagent storage.

5. The method as claimed in claim 1, in which the automated analysis device comprises a storage container for a consumable and/or a waste container and the system state is a load state of the storage container for a consumable and/or of the waste container.

6. The method as claimed in claim 1, in which the standby control unit is started up after a predetermined period of inactivity of the automated analysis device.

7. The method as claimed in claim 1, in which the standby control unit monitors a number of operating parameters for a deviation from a predetermined intended value.

8. A method for restoring an operating mode in an automated analysis device, which is operated in a standby mode using the method claimed in claim 7, wherein the method for restoring comprises:
   restarting the central control unit and
   loading the operating parameters monitored by the standby control unit into the central control unit.

9. The method as claimed in claim 8, in which identified deviations of the operating parameters from a predetermined intended value are indicated to a user.

10. The method as claimed in claim 9, in which the system state is reestablished by the central control unit following user input.

11. The method as claimed in claim 1, further comprising integrating the standby control unit into a housing of the DC hub.

12. An automated analysis device comprising a central control unit, an AC hub, a DC hub, a cooling unit, and a standby control unit; the AC hub coupled to provide AC power to the central control unit, the cooling unit, and the DC hub; the DC hub coupled to provide DC power to the standby control unit; the central control unit configured to operate the cooling unit; and the standby control unit configured to operate the cooling unit and monitor a number of operating parameters for a deviation from a predetermined value after the central control unit is shut down.

13. The automated analysis device as claimed in claim 12, wherein the standby control unit controls an electric switch which separates the central control unit from the AC hub.

14. The automated analysis device as claimed in claim 12 or 13, wherein the standby control unit is configured to monitor a temperature in the cooling unit.

15. The automated analysis device as claimed in claim 12, wherein the DC hub comprises a housing and the standby control unit is integrated into the housing.

16. The automated analysis device as claimed in claim 12, wherein the DC hub comprises a power supply unit connected to the standby control unit.

17. The automated analysis device as claimed in claim 12, wherein the central control unit comprises a personal computer.

18. The automated analysis device as claimed in claim 12, wherein the standby control unit comprises a printed circuit board with a microcontroller.

* * * * *